United States Patent
Sharp et al.

(10) Patent No.: US 9,376,509 B2
(45) Date of Patent: Jun. 28, 2016

(54) EXTENDED SURFACTANT FOR EMULSION POLYMERIZATION

(75) Inventors: Melanie Anne Sharp, Lake Charles, LA (US); Oliver Herzog, Geesthacht (DE); Sebastiano Giovanni Giordano, Casalpusterlengo (IT); Teresa Linville Marino, Sulphur, LA (US); Kip Douglas Sharp, Lake Charles, LA (US)

(73) Assignee: Sasol Performance Chemicals, GmbH (DE)

( * ) Notice: Subject to any disclaimer, the term of this patent is extended or adjusted under 35 U.S.C. 154(b) by 0 days.

(21) Appl. No.: 14/239,478

(22) PCT Filed: Aug. 24, 2012

(86) PCT No.: PCT/US2012/052212
§ 371 (c)(1),
(2), (4) Date: Mar. 28, 2014

(87) PCT Pub. No.: WO2013/028950
PCT Pub. Date: Feb. 28, 2013

(65) Prior Publication Data
US 2014/0228530 A1    Aug. 14, 2014

Related U.S. Application Data

(60) Provisional application No. 61/526,958, filed on Aug. 24, 2011.

(51) Int. Cl.
| | | |
|---|---|---|
| *C08F 2/26* | (2006.01) | |
| *C07C 309/10* | (2006.01) | |
| *C08F 218/08* | (2006.01) | |
| *C08K 5/41* | (2006.01) | |
| *C08F 220/18* | (2006.01) | |

(52) U.S. Cl.
CPC ............... *C08F 2/26* (2013.01); *C07C 309/10* (2013.01); *C08F 218/08* (2013.01); *C08F 220/18* (2013.01); *C08K 5/41* (2013.01)

(58) Field of Classification Search
CPC .......... C08F 2/26; C08F 218/08; C08F 220/18
USPC .................................................. 526/110, 209
See application file for complete search history.

(56) References Cited

U.S. PATENT DOCUMENTS

| | | | |
|---|---|---|---|
| 6,380,302 B1 * | 4/2002 | Ikenaga et al. ................ 524/747 |
| 2004/0048963 A1 | 3/2004 | Sawada | |
| 2008/0207939 A1 | 8/2008 | Tropsch et al. | |
| 2010/0305254 A1 | 12/2010 | Ikenaga | |

FOREIGN PATENT DOCUMENTS

| | | |
|---|---|---|
| DE | 102004007152 | 8/2005 |
| EP | 2455446 | 5/2012 |
| WO | WO2012/036700 | 3/2012 |

OTHER PUBLICATIONS

Wu et al, Branched Alkyl Alcohol Propoxylated Sulfate Surfactants for Improved Oil Recovery, Tenside Surf. Det. 47 (2010), pp. 152-161.*
Bushman et al., Surfactants for Environmental and Other Applications, IP.com electronic publication, Jan. 2004.
Wu et al., Branched Alkyl Alcohol Propoxylated Sulfate Surfactants for Improved Oil Recovery, Tenside Surf. Det. 47 (2010) 3, pp. 152-161.

* cited by examiner

*Primary Examiner* — Robert Harlan
(74) *Attorney, Agent, or Firm* — Bushman Werner, P.C.

(57) ABSTRACT

An extended anionic surfactant having the general formula:

RO—(PO)$n$-YZ wherein R is a linear alkyl chain ranging from C6 to C36, a branched alkyl chain ranging from C6 to C36, or a mixture thereof;
PO is a propyleneoxy group;
Y is —SO$_3$, —CH$_2$CH$_2$CH$_2$—SO$_3$, —CH$_2$CH(CH$_3$)—SO$_3$, or —CH$_2$COO;
Z is a cation; and
n is 1 to 50.

10 Claims, No Drawings

EXTENDED SURFACTANT FOR EMULSION POLYMERIZATION

CROSS REFERENCE TO RELATED APPLICATION

This application is a national phase of International Application PCT/US2012/052212, filed Aug. 24, 2012, which claims priority to U.S. Application No. 61/526,958 filed on Aug. 24, 2011 the disclosures of which are incorporated herein by reference for all purposes.

FIELD OF THE INVENTION

The present invention relates to emulsion polymerization and more specifically to a surfactant for use in such polymerization processes.

DESCRIPTION OF THE PRIOR ART

Emulsion polymerization requires the use of surfactants to stabilize monomer droplets and to form the micelles where the polymerization of the monomers will take place. Without the addition of an appropriate surfactant, the monomers will coagulate and fall out of solution leading to unusable material.

Two types of surfactants are commonly used in emulsion polymerization: anionic and nonionic. As is well known to those of skill in the art, anionic surfactants are more frequently used than nonionic surfactants. Examples of anionic surfactants that have been used for emulsion polymerization include polyoxyethylene alkylphenyl ether sulfates, alkylbenzene sulfonates, polyoxyethylene alkyl ether sulfates, and alkyl sulfates. The polyoxyethylene alkylphenyl ether sulfates are utilized frequently in emulsion polymerization, but due to environmental issues, these materials are being phased out of use. In particular, companies engaged in emulsion polymerization are looking to alternative anionic surfactants and, in particular, for anionic surfactants to replace polyoxyethylene alkylphenyl ether sulfates, one of the most widely used surfactants.

One of the reasons for the use of the polyoxyethylene alkylphenyl ether sulfates was their cost effectiveness and their ability to provide improved particle stability over a wide range of thermo, mechanical, and electrolyte conditions. However, despite these advantages, their use has begun to decline. The declining use of these types of surfactants is not only due to governmental pressure but also the fact that large merchandisers are now demanding more green products.

SUMMARY OF THE INVENTION

In one aspect, the present invention provides a surfactant for use in emulsion polymerization.

In another aspect, the present invention provides a surfactant for use in emulsion polymerization processes that exhibits low-foaming and requires low dosages while maintaining micelle stability compared to typical anionic surfactants used in emulsion polymerization.

In a further aspect, the present invention provides a method for the production of a polymer emulsion through polymerization of a monomer in the presence of the surfactant of the present invention.

These and further features and advantages of the present invention will become apparent from the following detailed description.

DETAILED DESCRIPTION OF PREFERRED EMBODIMENTS

As used herein, the term "linear alkyl chain" refers to an alkyl chain with no branches. The term "branched alkyl chain" refers to an alkyl chain with one or more branches, including alkyl chains with linear portions and branched portions.

In accordance with the present invention, there is provided an extended anionic surfactant having the general formula:

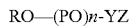

RO—(PO)$_n$-YZ wherein R is a linear alkyl chain ranging from C6 to C36, a branched alkyl chain ranging from C6 to C36, or a mixture thereof;
PO is a propyleneoxy group;
Y is —SO$_3$, —CH$_2$CH$_2$CH$_2$—SO$_3$, —CH$_2$CH(CH$_3$)—SO$_3$, or —CH$_2$COO;
Z is a cation; and
n is 1 to 50.

In a preferred embodiment, R is a mixture of linear and branched alkyl chains comprised of 9 to 17 carbon atoms. The branching of R can occur in any of the C2 to C(X−1) positions, wherein X is the number of carbon atoms in the alkyl chains. Preferably X is 9 to 17. Most preferably the branching is in the C2 position. The number of alkyl branches of R can range from 0 to 7, but is preferably from 0 to 4, and more preferably from 0 to 3. The length of the branches is preferably from 1 to 8 carbon atoms. The value of n is preferably 2 to 10, and more preferably 4 to 8. The cation is the counterion to the anionic group. The cation could be, but is not limited to: sodium, potassium, ammonium, monoethanolamine, diethanolamine, triethanolamine, or magnesium.

Emulsion polymerization is a type of radical polymerization that typically starts with an emulsion incorporating water, monomer and surfactant. The most common type of emulsion polymerization is an oil-in-water emulsion, in which drops of a monomer (the oil) are emulsified with surfactants in a continuous phase of water. Water soluble polymers such as certain polyvinyl alcohols or hydroxyethyl celluloses can also be used to act as emulsifiers/stabilizers.

In emulsion polymerization, initiation is the first step. During initiation, an active center is created from which a polymer chain is generated. As is well known, not all monomers are susceptible to all types of initiators. Radical initiation works best on the carbon-carbon double bond of vinyl monomers and the carbon-oxygen double bond in aldehydes and ketones.

A wide variety of initiators can be used in emulsion polymerization. Non-limiting examples include organic peroxides or azo-compounds, metal iodides, metal alkyls, persulfates, as well as various techniques such as ionizing radiation, electrochemical or electrolysis, stolification, etc. In emulsion polymerization, there is also typically employed a termination mixture and finishing mixture, as is well known to those skilled in the art.

To demonstrate the utility of the surfactant of the present invention in a typical emulsion polymerization reaction, the following non-limiting examples are presented.

EXAMPLE 1

This example shows emulsion polymerization of butyl acrylate (BA) and of vinyl acetate (VA). The mixtures and solutions are shown in Table 1 below. The aqueous mixture (A) was charged into the reactor. This was heated under stirring at 72-80° C. The initiator solution (B) was then added.

The mixture of monomers (C) was added dropwise to the reactor over 4 hours while maintaining the temperature at approximately 75° C. The surfactants and monomers tested are shown in Table 2. The temperature was maintained 70-80° C. for an additional fifteen minutes. The termination mixture (D) was then added over 30 minutes. The mixture was allowed to cool down to 40° C. and the finishing mixture (E) was then added.

TABLE 1

| Ingredients | Weight (g) |
|---|---|
| A. Aqueous Mixture | |
| Water | 476 |
| Hydroxyethyl cellulose | 13 |
| Non-ionic surfactant[a] | 19.8 |
| Sodium bicarbonate | 1.5 |
| B. Initiator Solution | |
| Water | 3.30 |
| Ammonium persulfate | 1.1 |
| Anionic surfactant[a] | 1.8 |
| C. Monomers Mixture | |
| Butyl acrylate (BA) | 108 |
| Vinyl acetate (VA) | 372 |
| D. Termination Mixture | |
| Ammonium persulfate | 0.2 |
| Water | 2.5 |
| E. Finishing Mixture | |
| Ammonia[b] | 0.15 |
| Formaldehyde[c] | 1.8 |
| TOTAL WEIGHT | 1001.15 |

[a]calculate on 100% of active matter
[b]at 27% in aqueous solution
[c]at 30% in aqueous solution

TABLE 2

| | Reaction 041110 | Reaction 091110 | Reaction 161110 | Reaction 011210 |
|---|---|---|---|---|
| Monomers | BA/VA | BA/VA | BA/VA | BA/VA |
| Anionic Surfactant | DACLOR® 272023[1] | DACLOR® 272023 | DACLOR® 272023 | ALFOTERRA® 123-8-S[2] |
| Non-Ionic Surfactant | EMULDAC® AS/25[3] | EMULDAC® ALCS/100[4] | ISALCHEM® 11-21[5] | EMULDAC® ALCS/100 |

[1]A 27% active solution of the sodium salt of C1213 alcohol ethoxylated and sulfated in water from Sasol Italy.
[2]A surfactant according to the present invention. A 27% active solution of the sodium salt of a C1213 alcohol propoxylated with 8 moles of propylene oxide and sulfated.
[3]C1618 alcohol ethoxylated from Sasol Italy.
[4]C1618 alcohol ethoxylated from Sasol Italy.
[5]C11 alcohol ethoxylated from Sasol Italy.

The appearance, pH, and dynamic viscosity of the resulting polymerizations were measured. The results are shown in Table 3.

TABLE 3

| Analytic Parameter | Reaction 041110 | Reaction 091110 | Reaction 161110 | Reaction 011210 |
|---|---|---|---|---|
| Appearance at 25° C. | WHE[*] | WHE[*] | WHE[*] | WHE[*] |
| Dry residue at 150° C. | 50.9% | 50.4% | 50.7% | 51.5% |
| pH (1% dispersion in water) | 4.5 | 4.6 | 4.5 | 4.4 |
| ph (10% dispersion in water) | 4.4 | 4.6 | 4.5 | 4.5 |
| Dynamic viscosity[6] | 700 mPa*s | 4000 mPa*s | 6000 mPa*s | 5800 mPa*s |
| Dynamic viscosity[7] | 2200 mPa*s | 1200 mPa*s | 2120 mPa*s | 1890 mPa*s |
| Dynamic viscosity[8] | 3600 mPa*s | 2060 mPa*s | 3430 mPa*s | 3180 mPa*s |

[*]White Homogeneous Emulsion
[6]Brookfield DV II + Viscosimeter (25° C., 20 rpm, spindle No5)
[7]Rotational Haake Viscosimeter (25° C., 20 rpm)
[8]Rotational Haake Viscosimeter (25° C., 10 rpm)

EXAMPLE 2

This example shows an adhesive all-acrylic emulsion polymerization. The emulsion polymerization is set up using a one liter reaction vessel and five-port lid. The system is interfaced with a computer program containing controls for a nitrogen purge, temperature readouts and controls, addition ports for a balance and systolic pump feed, and a syringe pump feed. It also allows for the use of a motor driven stirrer. A condenser cools any vapors before vented. The kettle is wrapped with an insulator and heating mantle.

All materials other than the anionic surfactants were obtained from Aldrich and used "as is." The surfactants tested can be seen in Table 4. The DISPONIL® FES 27A and DOWFAX® 2A1 were combined for Competitive Sample 1. SURFACTANT 1 was used for Sample 1. The solids of each surfactant were accounted for by adjusting the DI water amount utilized.

TABLE 4

| Sample | Surfactant | Appearance |
|---|---|---|
| Competitive Sample 1 | DISPONIL® FES 27A[9] DOWFAX® 2A1[10] | Clear Liquid Clear Yellow Liquid |
| Sample 1 | SURFACTANT 1[11] | Clear Liquid |

[9]Lauryl 2 mole ether sulfate sodium salt which is considered an industry standard anionic surfactant, marketed by BASF.
[10]Alkyldiphenyloxide disulfonate, considered an industry standard anionic surfactant, marketed by Dow Chemicals.
[11]4 mole propoxy ether sulfate sodium salt of ISALCHEM® 123 alcohol, marketed by Sasol.

Prior to startup an initiating solution (kettle charge) containing high purity DI water, a polystyrene seed, and sodium peroxodisulfate was added to the vessel. The remaining materials including the surfactant, acid, and monomers were then mixed with an overhead mixer for 30 seconds to pre-emulsify the starting materials. This pre-emulsion was then put into a feed bottle on the balance with an empty feed line (of a previously determined volume) into the port. A second feed solution of a 7% active sodium peroxodisulfate solution was also set up in a syringe on a pump ready to deliver during the same delivery time as the pre-emulsion. The syringe also contained an additional 5 mLs to use as a "chaser." This would ensure complete reaction of the monomers after the addition of the pre-emulsion. The adhesive acrylic formulation is shown in Table 5.

TABLE 5

| Ingredients | Weight (g) |
| --- | --- |
| Kettle Charge | |
| Water | 84.1 |
| Polystyrene Seed | 0.73 |
| Feed 2 | 1.80 |
| (Amt to start in Kettle) | (86.63) |
| Feed 1. Pre-Emulsion | |
| Deionized Water | 174.09 |
| Surfactant | 9.44 |
| Acrylic Acid | 3.00 |
| n-Butyl Acrylate | 27.00 |
| 2-Ethylhexyl acrylate | 270.00 |
| Subtotal | 483.53 |
| Feed 2. | |
| Sodium peroxodisulfate (7% soln) | 9.00 |
| Post Add "chaser" | |
| Sodium peroxodisulfate (7% soln) | 5.0 |
| Total | 584.16 |

The reactor was set to heat to 75° C. at a rate of two degrees per minute with the stirrer set at 300 rpm. Nitrogen purged the reactor continuously throughout the addition stages and cook down. Once the temperature stabilized, the stirrer speed was increased to 500 rpm, and the pre-emulsion and initiator feeds were gradually added over a three hour time span. The "chaser" was then introduced via syringe pump over a ten minute interval. The emulsion remained stirring for an additional one hour at temperature (the "cook down" period). The vessel was then cooled to 35° C., and the stirrer speed was reduced to 200 rpm.

Following the cool down period, the contents of the vessel were then poured through a 190 mesh Gardner filter and dried in a vacuum oven to remove the water. From this the percent coagulum was calculated gravimetrically. Next, the coagulum-free latex was analyzed for percent solids by drying overnight in a vacuum oven and particle size analysis on a Malvern Zetasizer particle size analyzer. For each surfactant several runs were performed. The results of the percent coagulum, percent solids, and particle size are reported in Table 6.

TABLE 6

| Sample | Surfactant | Amount (g) in Formulation | Particle Size (nm) | Percent Coagulum | Percent Solids |
| --- | --- | --- | --- | --- | --- |
| Competitive Sample 1 | DISPONIL ® FES 27A | 5.35 | 467 | 0.04 | 48 |
|  | DOWFAX ® 2A1 | 4.09 | | | |
| Sample 1 | SURFACTANT 1 | 4.72 | 481 | 0.05 | 52 |

EXAMPLE 3

This example shows a latex acrylic emulsion polymerization. The emulsion polymerization is set up using a one liter reaction vessel and five-port lid. The system is interfaced with a computer program containing controls for a nitrogen purge, temperature readouts and controls, addition ports for a balance and systolic pump feed, and a syringe pump feed. It also allows for the use of a motor driven stirrer. A condenser cools any vapors before vented. The kettle is wrapped with an insulator and heating mantle.

All materials other than the anionic surfactants were obtained from Aldrich and used as is. The surfactants tested can be seen in Table 7. ABEX® EP-100 is Competitive Sample 1. SURFACTANT 1 was used as Sample 1 and using only 50% of the SURFACTANT 1 was Sample 2. Next, SURFACTANT 2 was used as Sample 3. RHODAPEX® EST30/SBL is Competitive Sample 2. The solids of each surfactant was accounted by adjusting the DI water amount utilized.

TABLE 7

| Sample | Surfactant | Appearance |
| --- | --- | --- |
| Competitive Sample 1 | ABEX ® EP-100[12] | Clear Liquid |
| Sample 1 | SURFACTANT 1[13] | Clear Liquid |
| Sample 2 | SURFACTANT 1[14] at half concentration | Clear Liquid |
| Sample 3 | SURFACTANT 2[15] | Slightly Yellow Liquid |
| Competitive Sample 2 | RHODAPEX ® EST30/SBL[16] | Slightly Yellow Liquid |

[12]Nonylphenol 4 mole ether sulfate ammonium salt, considered an industry standard anionic surfactant, marketed by Rhodia.
[13]Four mole propoxy ether sulfate sodium salt of ISALCHEM ® 123, marketed by Sasol.
[14]Four mole propoxy ether sulfate sodium salt of ISALCHEM ® 123, marketed by Sasol.
[15]Four mole propoxy ether sulfate sodium salt of ALFOL ® 12, marketed by Sasol.
[16]An isotridecyl ether sulfate sodium salt (alkylphenol ethoxylate free alternative) to ABEX ® EP-100, marketed by Rhodia Prior to startup an initiating solution (kettle charge) containing high purity DI water and ammonium persulfate was added to the vessel. The remaining materials including the surfactant, initiator, acid, and monomers were then mixed with an overhead mixer for 30 seconds to pre-emulsify the starting materials. This pre-emulsion was then put into a feed bottle on the balance with an empty feed line (of a previously determined volume) into the port. A post-add solution of ammonium sulfate and water was also set up in a syringe on a pump ready to deliver as a "chaser." This would ensure complete reaction of the monomers after the addition of the pre-emulsion. The all-acrylic latex formulation is shown in Table 8.

TABLE 8

| Ingredients | Weight (g) |
|---|---|
| Kettle Charge | |
| Water | 102.1 |
| Ammonium persulfate | 1.80 |
| (Amt to start in Kettle) | (104.31) |
| Pre-emulsion | |
| Deionized Water | 142.32 |
| Surfactant | 3.00 |
| Ammonium Persulfate | 0.75 |
| 2-Hydroxy Ethyl Acrylate | 6.00 |
| Acrylic Acid | 3.00 |
| n-Butyl Acrylate | 131.00 |
| Methyl Methacrylate | 160.00 |
| Subtotal | 446.07 |
| Total | 550.38 |
| Post Add "chaser" | |
| Ammonium Persulfate | 3.35 mls (3.35% active) |

The reactor was set to heat to 80° C. at a rate of two degrees per minute with the stirrer set at 300 rpm. Nitrogen purged the reactor continuously until the addition stage of the pre-emulsion. Once the temperature had stabilized, the stirrer speed was increased to 500 rpm, and the pre-emulsion was gradually added over a four hour time span. The "chaser" was then introduced via syringe pump over a ten minute interval. The emulsion remained stirring for an additional one hour at temperature (the "cook-down" period). The vessel was then cooled to 35° C., and the stirrer speed was reduced to 300 rpm.

Following the cool down period, the contents of the vessel were then poured through a 190 mesh Gardner filter and dried in a vacuum oven to remove the water. From this the percent coagulum was calculated gravimetrically. Next, the coagulum-free latex was analyzed for particle size analysis on a Brookhaven Zeta Plus particle size analyzer. For each surfactant several runs were performed. The results of the percent coagulum and particle size are reported in Table 9.

TABLE 9

| | Surfactant | Amount (g) in Formulation | Particle Size (nm) | Percent Coagulum |
|---|---|---|---|---|
| Competitive Sample 1 | ABEX ® EP-100 | 3.00 | 409 | 0.08 |
| Sample 1 | SURFACTANT 1 | 3.00 | 436 | 0.09 |
| Sample 2 | SURFACTANT 1 (50%) | 1.50 | 436 | 0.06 |
| Sample 3 | SURFACTANT 2 | 3.00 | 462 | 0.08 |
| Competitive Sample 2 | RHODAPEX ® EST30/SBL | 3.00 | 489 | 0.10 |

It was observed that the anionic extended surfactant of the present invention exhibited superior properties such as low foaming, low dosage quantities needed and superior particle stability as compared to typical, anionic surfactants used in emulsion polymerization. One of the disadvantages of emulsion polymerization is that the surfactants tend to remain in the polymer or are difficult to remove. Accordingly, the property noted above of low dosage quantities needed for the surfactant of the present invention is important as it leads to far less contamination of the end product.

The surfactant of the present invention can be used in a wide variety of emulsion polymerization reactions. Without wanting to limit, in any way, the type of emulsion polymerization and/or monomers employed, the surfactant of the present invention can be used in the production of latexes for paints, coatings, rheology modifiers, adhesives, and synthetic rubber, among a wide variety of uses.

It will also be appreciated that virtually any monomer used in emulsion polymerization can be employed in the process of the present invention.

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. A method for the production of a polymer emulsion comprising:

reacting a monomer in the presence of a polymerization initiator and a surfactant composition for emulsion polymerization, said surfactant composition comprising the following formula:

RO—(PO)$n$-YZ wherein R is a branched alkyl chain ranging from C6 to C36, or a mixture of branched alkyl chains ranging from C6 to C36 and linear alkyl chains ranging from C6 to C36;

alkyl branching of R is in the C2 position;

PO is a propyleneoxy group;

Y is —SO$_3$;

Z is a cation; and n is 1 to 50.

2. The method of claim 1, wherein R is a mixture of linear and branched alkyl chains comprised of 9 to 17 atoms.

3. The method of claim 1, wherein R is a branched alkyl chain.

4. The method of claim 1, wherein the number of alkyl branches of R ranges from 1 to 7.

5. The method of claim 1, wherein the number of alkyl branches of R ranges from 1 to 4.

6. The method of claim 1, wherein the number of alkyl branches of R ranges from 1 to 3.

7. The method of claim 1, wherein the chain length of the alkyl branches of R is 1 to 8 carbons.

8. The method of claim 1, wherein n is 2 to 10.

9. The method of claim 1, wherein n is 4 to 8.

10. The method of claim 1, wherein the monomer is a vinyl monomer.

* * * * *